US005534499A

United States Patent [19]
Ansell

[11] Patent Number: 5,534,499
[45] Date of Patent: Jul. 9, 1996

[54] LIPOPHILIC DRUG DERIVATIVES FOR USE IN LIPOSOMES

[75] Inventor: Steve Ansell, Vancouver, Canada

[73] Assignee: The University of British Columbia, Vancouver, Canada

[21] Appl. No.: 246,010

[22] Filed: May 19, 1994

[51] Int. Cl.$^6$ .................. A61K 31/70; A61K 31/715; A61K 9/127

[52] U.S. Cl. .................. 514/25; 514/2; 514/34; 514/449; 514/463; 424/1.21; 424/450; 536/4.1; 536/6.4; 536/17.2; 536/18.1; 549/432; 549/510

[58] Field of Search .................. 514/2, 25, 34, 514/449, 463; 424/1.21, 450; 536/4.1, 6.4, 17.2, 18.1; 549/510, 432

[56] References Cited

U.S. PATENT DOCUMENTS

| | | | |
|---|---|---|---|
| 4,235,871 | 11/1980 | Papahadjopoulos et al. | 424/450 |
| 4,501,728 | 2/1985 | Geho et al. | 424/450 |
| 4,603,044 | 7/1986 | Geho et al. | 424/450 |
| 4,737,323 | 4/1988 | Martin et al. | 264/4.3 |
| 4,837,028 | 6/1989 | Allen | 424/1.21 |
| 4,957,773 | 9/1990 | Spencer et al. | 427/570 |
| 5,316,771 | 5/1994 | Barenholz et al. | 424/450 |
| 5,334,391 | 8/1994 | Clark et al. | 424/450 |
| 5,411,730 | 5/1995 | Kirpotin et al. | 424/322 |
| 5,415,869 | 5/1995 | Straubinger et al. | 424/450 |

FOREIGN PATENT DOCUMENTS

WO94/13324   6/1994   WIPO.

OTHER PUBLICATIONS

Holton, et al., *J. Am. Chem. Soc.* 116:1597–1601 (1994).
Nicolaou, et al., *Nature* 367:630–634 (1994).
McGuire, et al., *Ann. Int. Med.*, 111:273–279 (1989).
Holmes, et al., *J. Natl. Cancer Inst.*, 83:1797–1805 (1991).
Kohn, et al., *J. Natl. Cancer Inst.*, 86:18–24 (1994).
Kohn, et al., *American Society for Clinical Oncology*, 12, Abstract 814 (1993).
Deutsch, et al., *J. Med. Chem.* 32:788–792 (1989).
Nicolaou, et al., *Nature* 364:464–466 (1993).
Mathew, et al., *J. Med. Chem.* 35:145–151 (1992).
Sharma, et al., *Cancer Res.* 53:5877–5881 (1993).
Szoka, et al., *Ann. Rev. Biophys. Bioeng.* 9:467–508 (1980).
Hope, et al., *Chem. Phys. Lip.* 40:89–107 (1986).
Renneisen, et al., *J. Biol. Chem.*, 265:16337–16342 (1990).
Leonetti, et al., *Proc. Natl. Acad. Sci. (USA)* 87:2448–2451 (1990).
Juliano, *Biochem. Biophys. Res. Commun.* 63:651–658 (1975).

*Primary Examiner*—Gary L. Kunz
*Assistant Examiner*—Kathleen Kahler Fonda
*Attorney, Agent, or Firm*—Townsend and Towsend and Crew

[57] ABSTRACT

The present invention provides novel lipophilic drug derivatives which are capable of being formulated in liposomes or micelles. These drug derivatives are known therapeutic agents which are covalently attached to a fatty acid chain of a phospholipid, glyceride, ceramide or 1,2-diacyloxypropane-3-amine. The linkage between the therapeutic agent and the lipid is one which can be cleaved in vivo, allowing the therapeutic agent to be separated from the micellar or liposomal formulation.

19 Claims, No Drawings

LIPOPHILIC DRUG DERIVATIVES FOR USE IN LIPOSOMES

BACKGROUND OF THE INVENTION

A number of pharmaceutical agents and potential pharmaceutical agents suffer from poor aqueous solubility, which can hamper the development of suitable clinical formulations. One approach to solving this problem is by synthesizing new derivatives with more polar functionality to increase water solubility. However, the addition of polar functionality is often disadvantageous when the therapeutic agent is required to cross a membrane for activity.

Another approach to increasing water solubility is to synthesize prodrugs in which the therapeutic agent is conjugated to a carrier group which assists in solubilizing the therapeutic agent and which is then cleaved in situ to regenerate the therapeutic agent which is now better able to penetrate a given membrane.

More recently, new methods of formulating compounds have become available. In particular, formulations based on liposome technology are now of significant interest. Liposomes are vesicles comprised of concentrically ordered phospholipid bilayers which encapsulate an aqueous phase. They form spontaneously when phospholipids are exposed to aqueous solutions and can accommodate a variety of bioactive molecules. Liposomes have been used for the selective delivery of both pharmaceutical agents and imaging agents. Nevertheless, a number of pharmaceutical agents have proven difficult to formulate, even in liposomes.

Paclitaxel (Taxol®), compound 1, is a diterpene isolated from the bark of the Western (Pacific) yew, *Taxus brevifolia* and is representative of a new class of therapeutic agent having a taxane ring system. Paclitaxel and its analogs have been produced by partial synthesis from 10-deacetylbaccatin III, a precursor obtained from yew needles and twigs, and by total synthesis. See Holton, et al., *J. Am. Chem. Soc.* 116:1597–1601 (1994) and Nicolaou, et al., *Nature* 367:630 (1994). Paclitaxel has been demonstrated to possess antineoplastic activity. More recently, it has demonstrated efficacy in several human tumors in clinical trials. See McGuire, et al., *Ann. Int. Med.*, 111:273–279 (1989); Holmes, et al., *J. Natl. Cancer Inst.*, 83:1797–1805 (1991); Kohn et al., *J. Natl. Cancer Inst.*, 86:18–24 (1994); and Kohn, et al., *American Society for Clinical Oncology*, 12 (1993).

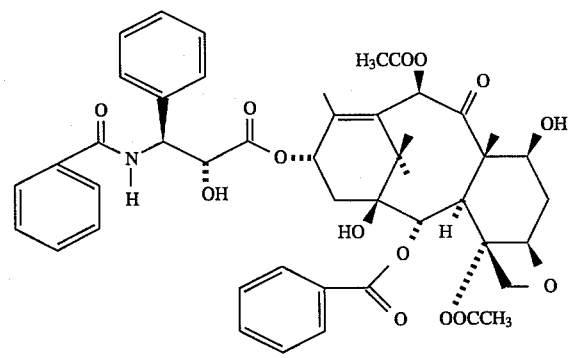

Taxol has proven difficult to formulate for therapeutic administration. Efforts to address the formulation problem have focused on synthesis of prodrugs and water-soluble analogs. See, Deutsch, et al., *J. Med. Chem.* 32:788–792 (1989), Nicolaou, et al., *Nature* 364:464–466 (1993) and Methew, et al., *J. Med. Chem.* 35:145–151 (1992). Attempts at liposomal formulations have also been difficult. See, Sharma, et al., *Cancer Res.* 53:5877–5881 (1993). Other classes of therapeutic agents suffer similar drawbacks. In particular, the family of podophyllotoxins, of which 2 is representative have also proven difficult to formulate.

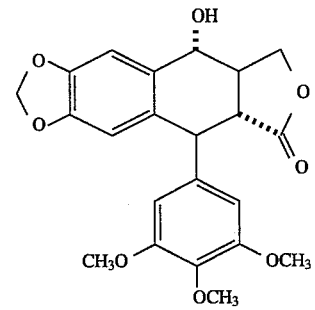

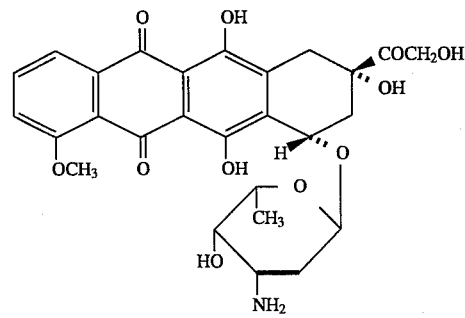

Still other classes of therapeutic agents, such as the daunomycin family of antibiotics (of which doxorubicin, 3, is representative) have been studied in liposomal formulations, but are hampered by such problems as limited affinity for the lipid bilayers. This results in compounds which are encapsulated entirely in the aqueous space and often have a tendency to leak out of the intraliposomal aqueous space.

What is needed are compounds which are designed for incorporation into the lipid bilayer and which can be easily formulated into liposomes and micelles. Moreover, the compounds should also act as prodrugs and ultimately result in a therapeutic agent which is free of any added functionality. Preferably, the approaches to the preparation of such compounds should have broad applicability to many classes of pharmaceutical agents.

Surprisingly, the present invention provides such compounds.

SUMMARY OF THE INVENTION

The present invention provides novel compounds which are capable of being formulated in liposomes or micelies. The compounds of the invention are therapeutic agents which are covalently attached to a fatty acid chain of a phospholipid, glyceride, ceramide or 1,2-diacyloxypropane-3-amine. The linkage between the therapeutic agent and the lipid is selected such that the therapeutic agent can be cleaved from the lipid in vivo.

The present invention further provides pharmaceutical compositions containing the novel lipophilic drug derivatives.

DETAILED DESCRIPTION OF THE INVENTION

The following abbreviations are used herein: DSPC, distearoyl phosphatidylcholine; HEPES, 4-(2-hydroxyethyl)- 1-piperazineethanesulfonic acid; BOC, tert-butoxycarbonyl; DCC, dicyclohexylcarbodiimide.

As used herein, the term "alkyl" refers to a saturated hydrocarbon radical which may be straight-chain or branched-chain (for example, ethyl, isopropyl, t-amyl, or 2,5-dimethylhexyl). When "alkyl" is used to refer to a linking group, it is taken to be a group having two available valences for covalent attachment, for example, —CH$_2$CH$_2$—, —CH$_2$CH$_2$CH$_2$—, —CH$_2$CH$_2$CH(CH$_3$)CH$_2$— and —CH$_2$(CH$_2$CH$_2$)$_2$CH$_2$—. Preferred alkyl groups as substituents are those containing 1 to 22 carbon atoms, with those containing 12 to 22 carbon atoms being particularly preferred. Preferred alkyl groups as linking groups are those containing 1 to 11 carbon atoms, with those containing 2 to 6 carbon atoms being particularly preferred. The term "lower alkyl" refers to alkyl groups having from 1 to 6 carbon atoms. The term "unsaturated alkyl" refers to alkyl groups having one or more double bonds or triple bonds. When "unsaturated alkyl" is used to refer to a linking group, it is taken to be a group having two available valences for covalent attachment, for example, —CH=CHCH$_2$—, —C≡CCH$_2$—, —CH$_2$CH=C(CH$_3$)CH$_2$— and —C≡C—(CH$_2$CH$_2$)$_2$CH$_2$—.

As used herein, the term "baselipid" refers to those lipids which are to be conjugated to therapeutic agents to prepare the compounds of the present invention. The term baselipid includes phospholipids, glycerides, ceramides and 1,2-diacyloxypropane-3-amines.

The term "acyl" refers to a radical produced from an organic acid by removal of the hydroxyl group. Examples of acyl radicals include acetyl, pentanoyl, palmitoyl, stearoyl, myristoyl, and caproyl.

The term "acyloxy" refers to a radical produced from an organic acid by removal of the acidic hydrogen atom. Examples of acyloxy radicals include acetoxy, pentanoxy, palmitoxy, and caproxy.

The term "oligosaccharide" refers to a carbohydrate that is made up of 2 to 10 monosaccharide units, which may be identical or different.

All ranges provided herein are inclusive of their upper and lower limits.

The present invention provides compounds which are capable of being formulated in liposomes or micelles and are represented by either formula I or formula II:

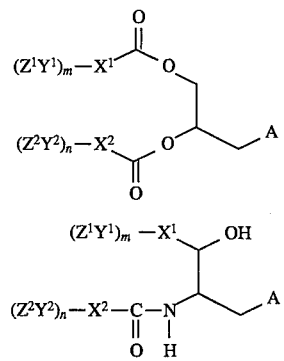

The group A is represents a variety of structures. These structures include a serine radical, an ethanolamine radical, a choline radical, a phosphocholine radical, a phosphoserine radical, a phosphoethanolamine radical, a glycerol radical, a phosphoglycerol radical, an inositol radical, a phosphoinositol radical, —NR$^1$R$^2$, —OCOR$^3$, —OH, —O—glucose, —O—galactose and —O—oligosaccharide wherein R and R$^2$ are each independently H or lower alkyl and R$^3$ is an alkyl or unsaturated alkyl radical.

The groups X$^1$ and X$^2$ in these formulas are the same or different, each being either an alkyl group, an unsaturated alkyl group, an alkyl linking group or an unsaturated alkyl linking group. When X$^1$ or X$^2$ is an alkyl or unsaturated alkyl group, they will preferably be from 11 to 23 carbon atoms in length. When X$^1$ or X$^2$ is an alkyl or unsaturated alkyl linking group, they will preferably be from 2 to 22 carbon atoms in length. The number of carbon atoms will be determined depending upon the length of the groups Y$^1$ and Y$^2$ such that the combination of X$^1$ with Y$^2$, or X$^2$ with Y$^2$ will have a length approximately equal to a carbon chain having from 6 to 23 carbon atoms. Additionally, when X$^1$ is an alkyl or unsaturated alkyl group, m will be zero. Similarly, when X$^2$ is an alkyl or unsaturated alkyl group, n will be zero.

The groups Y$^1$ and Y$^2$ in these formulas are likewise the same or different, each being either —S—, —NH—, —NHCO—, —CO(CH$_2$)$_p$CO$_2$—, —O—, =NNHCO—, —CO— and —CO(CH$_2$)$_p$CONH—, wherein p is an integer of from 0 to 8. The groups Y$^1$ and Y$^2$ are linking groups which provide a covalent attachment between the groups X$^1$ and Z$^1$, and X$^2$ and Z$^2$ respectively. In particular, the groups Y$^1$ and Y$^2$ will be selected depending upon the particular functionality in the therapeutic agent which is present and available for derivatization. For example, where a therapeutic agent, Z$^1$, has a hydroxyl group which can be derivatized to attach Z$^1$ to the baselipid, a suitable group Y$^1$ would be either —CO(CH$_2$)$_p$CO$_2$—, —CO— or —CO(CH$_2$)$_p$CONH—. Similarly, where a therapeutic agent, Z$^1$, has a sulfhydryl group which can be derivatized to attached the therapeutic agent to the baselipid, Y$^1$ would preferably be —S—, to form a disulfide linkage between Z$^1$ and X$^1$. Where the group to be derivatized is a carboxylic acid, Y$^1$ (or Y$^2$) is preferably —O— (to form an ester linkage) or —NH— (to form an amide linkage).

The groups Z$^1$ and Z$^2$ are also the same or different and, when present, are each a therapeutic agent. One of skill in the art will realize that virtually any therapeutic agent will be capable of derivatization into the lipophilic drug derivatives of the present invention. Typical therapeutic agents which are useful in the present invention are acyclovir, zidovudine, 2', 3'-dideoxycytidine, 2', 3'-dideoxyinosine, mitomycin C, 5-fluoro-2'-deoxyuridine, cytarabine (and other non-phosphorylated nucleoside drugs), dihydroartemisin, taxol, doxorubicin, podophyllotoxin, bleomycin, vinblastine, vincristine, cyclophosphamide, lomustine, semustine, cisplatin, procarbazine, and the retinoids. Preferred therapeutic agents are those from the taxol family of antineoplastic agents, the family of daunomycin antibiotics and the family of podophyllotoxins. Particularly preferred therapeutic agents are taxol and doxorubicin.

The symbols m and n are each integers of from 0 to 1, such that the sum of m+n is at least 1.

In one group of embodiments, the compound is of Formula I where A is a phosphocholine radical, a phosphoserine radical, a phosphoethanolamine radical, a phosphoglycerol radical or a phosphoinositol radical. In some further preferred embodiments, m is 0, X$^1$ is alkyl and Z$^2$ is taxol, doxorubicin or podophyllotoxin. In other further preferred embodiments, n is 0, X$^2$ is alkyl and Z$^1$ is taxol, doxorubicin or podophyllotoxin.

In another group of embodiments, the compound is of Formula I where A is —OCOR$^3$, —O—glucose, —O—galactose, or —O—oligosaccharide. In some further preferred embodiments, m is 0, $X^1$ is alkyl and $Z^2$ is taxol, doxorubicin or podophyllotoxin. In other further preferred embodiments, n is 0, $X^2$ is alkyl and $Z^1$ is taxol, doxorubicin or podophyllotoxin.

In still another group of embodiments, the compound is of Formula I where A is —$NR^1R^2$. In some further preferred embodiments, m is 0, $X^1$ is alkyl and $Z^2$ is taxol, doxorubicin or podophyllotoxin. In other further preferred embodiments, n is 0, $X^2$ is alkyl and $Z^1$ is taxol, doxorubicin or podophyllotoxin.

In yet another group of embodiments, the compound is of Formula II where A is a hydrogen, —O—glucose, —O—galactose, —O—oligosaccharide, phosphocholine radical, a phosphoserine radical, a phosphoethanolamine radical, a phosphoglycerol radical or a phosphoinositol radical. In some further preferred embodiments, m is 0, $X^1$ is alkyl and $Z^2$ is taxol, doxorubicin or podophyllotoxin. In other further preferred embodiments, n is 0, $X^2$ is alkyl and $Z^1$ is taxol, doxorubicin or podophyllotoxin.

The compounds of the present invention can be synthesized by methods which are well known to one of skill in the art. In general, therapeutic agents will be covalently attached to one or both of the acyl chains of a phospholipid, glyceride, ceramide or a 1,2-diacyloxypropane-3-amine. Conjugation of the drug to the baselipid can be effected using a crosslinker or by prior modification of the baselipid such that labile conjugates can be formed with functionalities commonly found in drugs (for example, hydroxyls, sulfhydryls, aldehydes, ketones, carboxylates and amines). The selection of an appropriate crosslinker or conjugating moiety will be guided by the functionality on the drug which is to be derivatized and on the particular conditions under which the drug will ultimately be cleaved from the baselipid. For example, if the drug is to be cleaved from the baselipid under acidic conditions such as those which exist in the lysosomal compartment of cells, an appropriate crosslinker would be a hydrazide baselipid which is covalently attached to an oxo group on a drug to form an acid sensitive hydrazone compound. When the drug is to be cleaved from the baselipid under alkaline conditions or under neutral conditions (by means of an esterase) an appropriate crosslinker would be a drug having a hydroxy group attached to a baselipid by means of an ester using a succinate crosslinker.

In one embodiment, compounds of formula I wherein A is a phosphocholine radical can be prepared beginning with the corresponding commercially available lysophosphatidylcholines of formula III.

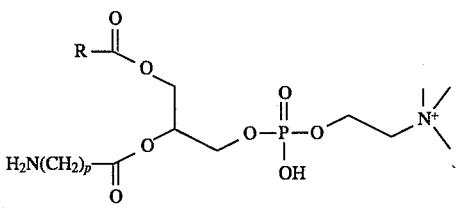

One of skill in the art can appreciate that other lysophosphatidyl compounds can be used as starting materials, including suitably protected lysophosphatidylethanolamine, lysophosphatidylglycerol, lysophosphatidylinositol and lysophosphatidylserine derivatives. In formula III, RC(O)— is a fatty acid radical which is typically lauroyl, myristoyl, palmitoyl, stearoyl, or oleoyl. Treatment of the lysophosphatidylcholine with a protected ω-aminoalkanoic acid in the presence of a coupling agent such as DCC, and subsequent removal of the protecting group provides a compound of formula IV.

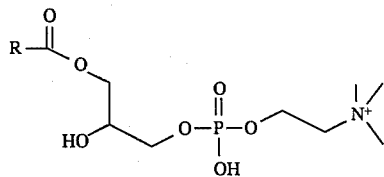

A number of protected and unprotected ω-aminoalkanoic acids are commercially available and can be used to prepare the compounds of the present invention. Examples of these amino acids are N-t-BOC-7-aminoheptanoic acid, N-t-BOC-6-aminohexanoic acid and 11-aminoundecanoic acid. Where the starting material is an unprotected amino acid, the amine functionality will typically be protected prior to further reactions. The nature of the protecting group in not critical but will be selected depending on conditions required for its attachment as well as for its removal. A preferred protecting group for amines is the tert-butoxycarbonyl group (BOC). This group can be attached to an amine using commercially available reagents such as di-t-butylpyrocarbonate and BOC-On. Examples of other suitable protecting groups can be found in Greene and Wuts, *Protecting Groups in Organic Synthesis*, Wiley-Interscience, Second Edition, (1991), incorporated herein by reference. After coupling the protected ω-amino acid to the lysophosphatidylcholine and removal of the protecting group, the primary amine will be acylated with a drug or a drug derivative. The nature of the drug derivative is not critical but will typically be a drug having an attached linking group such as a dicarboxylic acid. Reaction of a suitable drug having a reactive functionality (i.e., —OH) with a lower molecular weight dicarboxylic acid anhydride provides a drug having a tethered carboxylic acid. When the reactive functionality present on the drug is amino (—$NH_2$), reaction with cis-aconitic anhydride provides a drug having a suitable tethered carboxylic acid. A preferred drug derivative is taxol-2'-succinate (available from the treatment of taxol with succinic anhydride) which provides a compound of formula V.

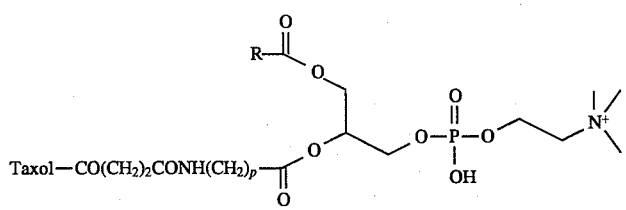

In another group of embodiments, lysophosphatidylcholines of formula III are acylated with a dicarboxylic acid to provide compounds of formula VI.

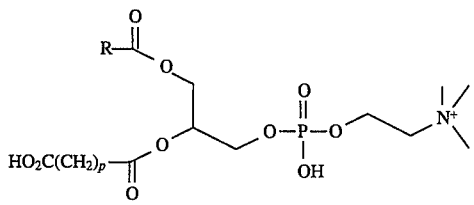

The size of the dicarboxylic acid is not critical but will typically be one wherein the carboxylic acid groups are linked together by an alkyl or unsaturated alkyl chain having from 2–20 carbon atoms, preferably about 8–14 carbon atoms. A number of dicarboxylic acids are commercially available, including 1,10-decanedicarboxylic acid, 1,12-dodecanedicarboxylic acid, hexadecanedioic acid, and suberic acid. After acylation of the lysophosphatidylcholine, the remaining carboxylic acid is converted to its acid hydrazide by treatment with hydrazinc. Subsequent treatment of these acid hydrazides with therapeutic agents having a ketone functionality (for example, doxorubicin) provides a hydrazone derivative of formula VII.

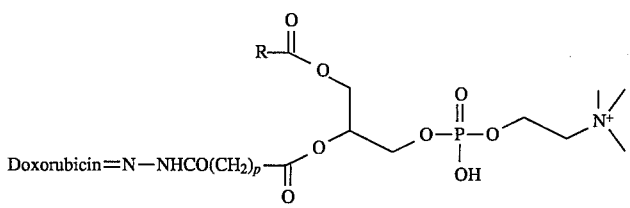

Compounds of formula I, wherein A is —NR$^1$R$^2$ can be prepared beginning with 3-dialkylamino-1,2-propanediols. For example, 3-(dimethylamino)-1,2-propanediol (Aldrich Chemical Company, Milwaukee, Wis., USA) can be used as a starting material for compounds of formula I wherein A is —N(CH$_3$)$_2$. Alternatively, 3-(dimethylamino)-1,2-propanediol can be prepared by treatment of glycidol with dimethylamine in ethanol. Subsequent treatment of 3-(dimethylamino)-1,2-propanediol with an acid chloride results in acylation of the primary hydroxyl group to provide compounds of formula VIII.

A number of acid chlorides are suitable, including those which are prepared from fatty acids such as caproic acid, decanoic acid, lauric acid, myristic acid, palmitic acid, stearic acid, or oleic acid. Subsequent acylation of the secondary hydroxyl with a protected amino acid such as those use above, and removal of the protecting group provides compounds of formula IX.

Acylation of the primary amino group with a suitable drug derivative can be carried out as described above, to provide compounds of formula X.

As is apparent to one of skill in the art, the steps required for acylating the primary and secondary hydroxyl groups of the starting material can be reversed if suitable steps are taken to first protect the primary hydroxyl group. Following acylation of the secondary hydroxyl group, the primary hydroxyl is deprotected and derivatized to provide compounds of formula XI which are also contemplated by the present invention.

Compounds of formula II, wherein A is —O—glucose, —O—galactose or —O—oligosaccharide can be synthesized in a manner similar to those described above beginning with a sphingosine analog having an attached sugar. For example, acylation of the secondary amine of 1-β-D-galactosylsphingosine (psychosine, Sigma Chemical Company, St. Louis, Mo., USA) with a dicarboxylic acid provides compounds of formula XII.

Conversion of the resultant carboxylic acid to an acid hydrazide followed by hydrazone formation with an appropriate therapeutic agent provides compounds of formula XIII (shown with Z=taxol).

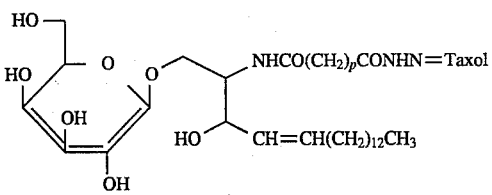

Alternatively, the secondary amine can be acylated with a protected ω-amino acid as described for the preparation of compounds of formula IV. Removal of the protecting group and acylation of the resultant amine with drug derivatives such as taxol-2'-succinate provides compounds of formula XIV.

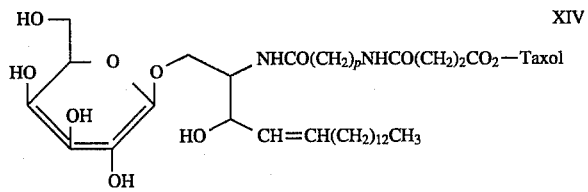

Compounds of formula I, wherein A is —OCOR³ can be prepared from commercially available 1,2- and 1,3-diacylglycerols. Preferred diacylglycerols are 1,2- and 1,3-dimyristin, 1,2-and 1,3-dioctanoylglycerol, 1,2-and 1,3-dioleoylglycerol, 1,2- and 1,3-dipalmitin, and 1,2- and 1,3-distearin (all from Sigma Chemical Company, St. Louis, Mo,, USA). Manipulation of the free hydroxyl group can be carried out as described above for the phosphatidyl derivatives to provide the desired compounds.

The present invention also provides pharmaceutical compositions comprising the compounds described above in micellar formulations and liposomal formulations. Typically, the compounds of the present invention will be incorporated into the carriers during formation of the micelles and liposomes.

Micelles containing the compounds of the present invention can be prepared by methods which are well known to one of skill in the art. The micellar formulations will typically include at least one lysophosphatidylcholine, lysophosphatidylethanolamine, lysophosphatidylserine, lysophosphatidylglycerol, phosphatidylethanolamine-polyoxyethylene conjugate, acyl-polyoxyethylene ester, alkyl-polyoxyethylene ether, polyoxyethylenesorbitan, phosphatidic acid-polyoxyethylene conjugate, alkyl pyranoside, or other pharmaceutically acceptable detergent. The alkyl pyranosides useful in the present invention include decyl-, dodecyl-, heptyl-, octyl-, nonyl-, undecyl-, and tetradecyl-glucopyranosides and maltosides. The polyoxyethylene conjugates which are used in the compositions of the present invention can be prepared by combining the conjugating group (i.e. phosphatidic acid or phosphatidylethanolamine) with an appropriately functionalized polyoxyethylene derivative. For example, phosphatidylethanolamine can be combined with polyoxyethylene bis(p-toluenesulfonate) to provide a phosphatidylethanolamine-polyoxyethylene conjugate.

Liposomes are formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream.

Typically, the major lipid component in the liposomes is phosphatidylcholine. Phosphatidylcholines having a variety of acyl chain groups of varying chain length and degree of saturation are available or may be isolated or synthesized by well-known techniques. In general, less saturated phosphatidylcholines are more easily sized, particularly when the liposomes must be sized below about 0.3 microns, for purposes of filter sterilization. Phosphatidylcholines containing saturated fatty acids with carbon chain lengths in the range of $C_{14}$ to $C_{22}$ are preferred. Phosphatidylcholines with mono or diunsaturated fatty acids and mixtures of saturated and unsaturated fatty acids may also be used. Other suitable lipids include phosphonolipids in which the fatty acids are linked to glycerol via ether linkages rather than ester linkages. Liposomes useful in the present invention may also be composed of sphingomyelin or phospholipids with head groups other than choline, such as ethanolamine, serine, glycerol and inositol. Liposomes useful in the present invention may also be composed of cholesterol, diglycerides, ceramides, phosphatidylethanolamine-polyoxyethylene conjugates and phosphatidic acid-polyoxyethylene conjugates. Preferred liposomes will include a sterol, preferably cholesterol, at molar ratios of from 0.1 to 1.0 (cholesterol:phospholipid). Most preferred liposome compositions are distearoylphosphatidylcholine/cholesterol, dipalmitoylphosphatidylcholine/cholesterol, and sphingomyelin/cholesterol. Methods used in sizing and filter-sterilizing liposomes are discussed below.

A variety of methods are available for preparing liposomes as described in, e.g., Szoka et al., Ann. Rev. Biophys. Bioeng. 9:467 (1980), U.S. Pat. Nos. 4,235,871, 4,501,728, 4,837,028, the text Liposomes, Marc J. Ostro, ed., Marcel Dekker, Inc., New York, 1983, Chapter 1, and Hope, et al., Chem. Phys. Lip. 40:89 (1986), all of which are incorporated herein by reference. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

Following liposome preparation, the liposomes may be sized to achieve a desired size range and relatively narrow distribution of liposome sizes. A size range of about 0.2–0.4 microns allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present inventions, liposomes having a size of from about 0.05 microns to about 0.15 microns are preferred.

In certain embodiments, it is desirable to target liposomes using targeting moieties that are specific to a particular cell type, tissue, and the like. Targeting of liposomes using a variety of targeting moieties (e.g., ligands, receptors and monoclonal antibodies) has been previously described (see, e.g., U.S. Pat. Nos. 4,957,773 and 4,603,044, both of which are incorporated herein by reference).

Examples of targeting moieties include monoclonal antibodies specific to antigens associated with neoplasms, such as prostate cancer specific antigert. Tumors can also be diagnosed by detecting gene products resulting from the activation or overexpression of oncogenes, such as ras or c-erB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV1) and papilloma virus antigens. Inflammation can be detected using molecules specifically recognized by surface molecules which are expressed at sites of inflammation such as integrins (e.g., VCAM-1), selectin recpetors (e.g., ELAM-1) and the like.

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see, Renneisen, et al., *J. Biol. Chem.*, 265:16337–16342 (1990) and Leonetti, et al., *Proc. Natl. Acad. Sci.* (USA) 87:2448–2451 (1990), both of which are incorporated herein by reference).

Targeting mechanisms generally require that the targeting agents be positioned on the surface of the liposome in such a manner that the target moieties are available for interaction with the target, for example, a cell surface receptor. The liposome is typically fashioned in such a way that a connector portion is first incorporated into the membrane at the time of forming the membrane. The connector portion must have a lipophilic portion which is firmly embedded and anchored in the membrane. It must also have a hydrophilic portion which is chemically available on the aqueous surface of the liposome. The hydrophilic portion is selected so that it will be chemically suitable to form a stable chemical bond with the targeting agent which is added later. Therefore, the connector molecule must have both a lipophilic anchor and a hydrophilic reactive group suitable for reacting with the target agent and holding the target agent in its correct position, extended out from the liposome's surface. In some cases it is possible to attach the target agent to the connector molecule directly, but in most instances it is more suitable to use a third molecule to act as a chemical bridge, thus linking the connector molecule which is in the membrane with the taxget agent which is extended, three dimensionally, off of the vesicle surface.

Pharmaceutical compositions comprising the liposomes and compounds of the invention are prepared according to standard techniques, as well as those techniques described above. Preferably, the pharmaceutical compositions are administered parenterally, i.e., intraanicularly, intravenously, subcutaneously, or intramuscularly. More preferably, the pharmaceutical compositions are administered intravenously by a bolus injection. Suitable formulations for use in the present invention are found in *Remington's Pharmaceutical Sciences*, Mack Publishing Company, Philadelphia, Pa., 17th ed. (1985).

Preferably, the pharmaceutical compositions are administered intravenously Thus, this invention provides compositions for intravenous administration which comprise a solution of the liposomes suspended in an acceptable carrier, preferably an aqueous carrier. A variety of aqueous carriers may be used, e.g., water, buffered water, 0.9% isotonic saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of liposomes, in the pharmaceutical formulations can vary widely, i.e., from less than about 0.05 %, usually at or at least about 2–5 % to as much as 10 to 30% by weight and will be selected primarily by fluid volumes, viscosities, etc., in accordance with the particular mode of administration selected.

Liposome charge is an important determinant in liposome clearance from the blood, with negatively charged liposomes being taken up more rapidly by the reticuloendothelial system (Juliano, *Biochem. Biophys. Res. Commun.* 63:65 1 (1975)) and thus having shorter half-lives in the bloodstream. Liposomes with prolonged circulation half-lives are typically desirable for therapeutic and diagnostic uses. For instance, liposomes which can be maintained from 8, 12, or up to 24 hours in the bloodstream are particularly preferred.

Additionally, the liposome suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The following examples are provided by way of illustration and not by way of limitation.

EXAMPLES

Materials

The reagents used in the following examples are commercially available or can be prepared by the methods cited. The starting lysophospholipids, including 1-oleoyl-2-hydroxy-L-α-phosphatidylcholine, were obtained from Avanti Polar Lipids, Inc. (Alabaster, Ala., USA). Egg phosphatidylcholine (EPC) and 1-stearoyl-L-α-phosphatidyl (SHPC) was obtained from Avanti Polar Lipids (Alabaster, Ala., USA). Triethylamine and trifluoroacetic acid were obtained from Fischer Scientific (Ottowa, Ontario, Canada). Stearic acid and 3-N,N-dimethylaminopropan-1,2-diol were obtained form Aldrich Chemical Company (Milwaukee, Wis., USA). Oxalyl chloride, flourescamine, N-hydroxysuccinimide, 4-N,N-dimethylamino pyridine, dicyclohexylcarbodiimide, 11-aminoundecanoic acid, and di-tert-butyl pyrocarbonate were obtained from Sigma Chemical Company (St. Louis, Mo., USA). HEPES (N-( 2-hydroxymethyl)piperazine-N'-(2-ethanesulfonic acid)) (from Sigma Chemical Co.) buffered saline (HBS) was prepared as follows: A solution of HEPES (4.77 g) and sodium chloride (8.77 g) in distilled water (1 L) was adjusted to pH 7.4 using 5M sodium hydroxide solution. A number of ω-amino acids are commercially available and can be protected as their BOC derivatives. The following method is illustrative of the conditions employed to prepare BOC-amino acids.

Synthesis of N-t-BOC-11-aminoundecanoic Acid (BADA)

Di-tert-butyl pyrocarbonate (26 g) was added to a solution of 11-aminoundecanoic acid (25 g) and sodium hydroxide (7 g) in methanol (100 mL). The reaction mixture was stirred at room temperature overnight. The solution was then filtered, diluted with water, acidified with dilute hydrochloric acid and the resultant suspension was extracted with methylene chloride. The organic fractions were dried over magnesium sulphate, filtered and the solvent was removed under reduced pressure. The resultant crystalline solid was broken up and dried on a lyophilizer, to provide N-t- BOC-11-aminoundecanoic acid as a white powder (33 g). This material was used in the following reactions without further purification.

Example I

This example illustrates the synthesis of 1-oleoyl-2-(N-(4'-O-(2"-taxyl)-succinoyl)-11-aminoundecanoyl)-L-α-phosphatidylcholine (OTSAUPC).

extracted with chloroform. TLC analysis indicated that about half of the OHPC had reacted. The organic fraction was dried, filtered and the solvent was evaporated. The residue was again treated with BAD A (0.60 g) and DCC (0.20 g) in chloroform, and stirred at room temperature overnight. The reaction mixture was treated as before. The residue was subjected to column chromatography on silica gel (mesh 70–230 ASTM, 20 g) using methanol in methylene chloride as the eluent (250 mL of 20% MeOH followed by 250 mL of 50% MeOH). Fractions containing the product were combined and the solvent was removed. The residue was taken up in water, centrifuged and the supernatant was dialyzed against distilled water overnight. The aqueous solution was lyophilized to provide OBADPC as a gummy white powder (0.49 g). The identity of the material was confirmed by $^1$H NMR.

B. Conversion of OBADPC to OTSAUPC

OBADPC (110 mg) was treated with triflouracetic acid (1 mL) for thirty minutes at room temperature. The triflouracetic acid was removed under a nitrogen stream and the residue was neutralized with excess sodium hydrogen carbonate and water. The solution was diluted with water and extracted with methylene chloride (ethanol was required to break the emulsion). The solvent was removed under reduced pressure and the residue was dried by azeotropic distillation under vacuum with ethanol (2X), to provide crude 1-oleoyl-2-( 11-aminoundecanoyl)-L-α-phosphatidylcholine (OAUPC) as a yellow oil. TLC analysis indicated a single polar component (OAUPC) containing a free amino group (detected with flourescamine in acetone) together with traces of OBAPBC. Taxol-2'-succinate (prepared according to this procedure of Deutsch et al. *J. Med. Chem.*, 32:788–792 (1989), and incorporated herein by reference) (52 rag), DCC (12 mg) and N-hydroxysuccinimide (9 mg) in methylene

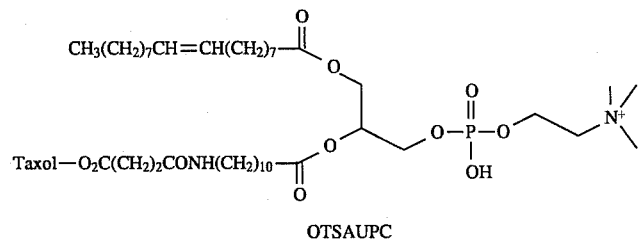

OTSAUPC

A. Synthesis of 1-oleoyl-2-(N-t-BOC-11-aminoundecanoyl)-L-α-phosphatidylcholine (OBADPC)

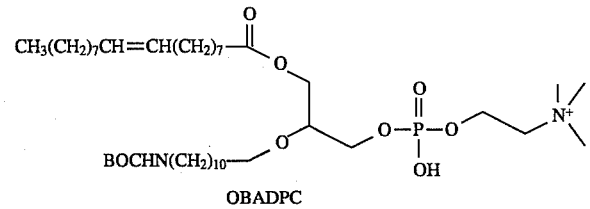

OBADPC

A solution of 1-oleoyl-2-hydroxy-L-α-phosphatidylcholine (OHPC, 0.50 g), N-t-BOC-11-aminoundecanoic acid (BADA, 0.60 g), dicyclohexylcarbodiimide (DCC, 0.20 g) and 4-N,N-dimethylaminopyridine (DMAP, 0.20 g) in alcohol free chloroform (50 mL) was stirred at room temperature overnight. The solution was diluted with water, acidified and chloride (1 mL) was stirred at room temperature for one hour. A solution of the crude OAUPC (78 mg) in methylene chloride (1 mL) was added and the reaction mixture was stirred for one hour. Triethylamine (4 drops) was then added and the reaction mixture was stirred for an additional two hours. The solution was filtered, diluted with dilute hydrochloric acid and extracted with methylene chloride. The combined organic extracts were washed with distilled water and the solvent was removed under a nitrogen stream. The residue was passed down a Pasteur pipette column containing silica gel and using methanol/methylene chloride (5 mL of 10% MeOH, then 10 mL of 50% MeOH followed by a 100% methanol flush) as the eluent. Fractions containing the product were combined and evaporated to provide OTSAUPC as a colorless glass (60 mg).

Example 2

This example illustrates the synthesis of 1-stearoyl-2-(N-(4'-O-(2"-taxyl)-succinoyl)- 11-aminoundecanoyl)-3-N,N- dimethylaminopropane (STDAP).

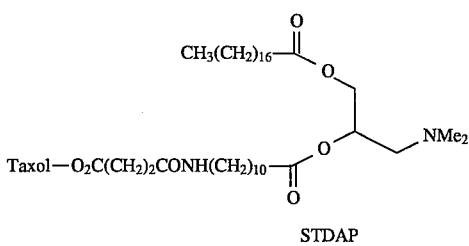

STDAP

A. Synthesis of
1-stearoyl-2-hydroxy-3-N,N-dimethylaminopropane
(SHDAP)

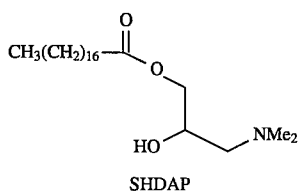

SHDAP

A solution of stearic acid (1 g) in benzene (100 mL) was treated with oxalyl chloride (6 mL) at room temperature for one hour. The solvent was removed under reduced pressure and the residue was dissolved in dry THF. The solution was cooled to 0° C. and slowly added to a solution of 3-N,N-dimethylaminopropan-1,2-diol, with stirring. The reaction mixture was stirred at 0° C. for 0.5 hour and then warmed to room temperature for two hours. The resulting solution was diluted with water, made basic with sodium hydroxide and extracted with methylene chloride. The organic extract was concentrated and chromatographed to provide SHDAP (0.39 g).

B. Synthesis of
1-stearoyl-2-(11-aminoundecanoyl)-3-N,N-dimethylaminopropane (SAUDAP)

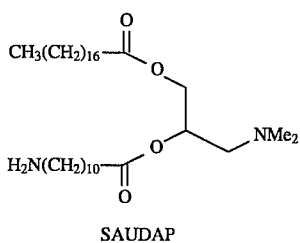

SAUDAP

A solution of SHDAP (0.39 g), BADA (0.64 g), DCC (0.26 g) and DMAP (0.12 g) in alcohol free chloroform (20 mL) was stirred at room temperature overnight. The reaction mixture was filtered, diluted with water, acidified and extracted with methylene chloride. The organic fractions were dried and the residue was treated with triflouroacetic acid (2 mL) at room temperature for 0.5 hour. The mixture was diluted with water, neutralized with sodium bicarbonate and extracted with methylene chloride. The organic fractions were dried and the residue was chromatographed on silica gel (32 g) using 15% methanol in methylene chloride as eluant, to provide SAUDAP as a colorless oil (0.15 g).

C. Conversion of SAUDAP to STDAP

A solution of SAUDAP (10 mg), taxol-2'-succinate (10 mg), DCC (6 mg), DMAP (10 mg) and N-hydroxysuccinimide (10 mg) in methylene chloride was stirred at room temperature for two hours. The reaction mixture was diluted with water, acidified with dilute hydrochloric acid and extracted with methylene chloride. The combined organic extracts were dried over magnesium sulphate, filtered and the solvent was removed under a nitrogen stream. The residue was chromatographed on a preparative TLC plate using 4% methanol in methylene chloride as the eluent. The major taxol component was located using fluorescent light and extracted with 50/50 methanol/methylene chloride to provide STDAP as a colorless glass.

Example 3

This example illustrates the protocol for formulating lipophilic taxol into micelles and liposomes.

A. Miceliar Fomulation of OTSAUPC with SHPC

A mixture of OTSAUPC (1 mg) and SHPC (5 mg) was suspended in distilled water and vortexed for ten minutes, to provide a clear solution. The micellar solution was centrifuged at 3000 rpm for thirty minutes. No material pelleted out.

B. Liposomal Formulation of OTSAUPC with SHPC and EPC

A mixture of OTSAUPC (3.2 mg), EPC (26.4 mg) and SHPC (2.2 mg) was dissolved in 10% methanol in benzene and then lyophilized. The resultant powder was dispersed in HBS (1 mL) and extruded ten times through two stacked polycarbonate filters (100 nm pore size, from Poretics Corp., Livermore, Calif., USA) using a T001 extruder (Lipex Biomembranes, Vancouver, British Columbia, USA). Particle sizing of the resultant solution using a Nicomp model 270 submicron particle sizer indicated a mean vesicle diameter of 90 nm.

C. Liposomal Formulation of OTSAUPC with EPC

A mixture of OTSAUPC (3.2 mg) and EPC (26.4 mg) was dissolved in 10% methanol in benzene and then lyophilized. The resultant powder was dispersed in HBS (1 mL) and extruded ten times through two stacked polycarbonate filters (100 nm pore size) using a T001 extruder. Particle sizing of the resultant solution using a Nicomp model 270 submicron particle sizer indicated a mean vesicle diameter of 91 nm.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pharmaceutical compound for use in liposome and micellar formulations, said compound being a member selected from the group consisting of compounds of formula I and compounds of formula II:

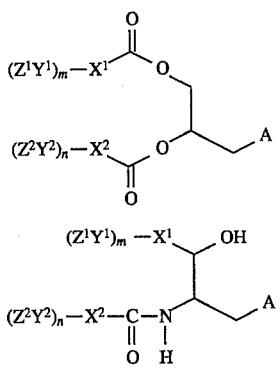

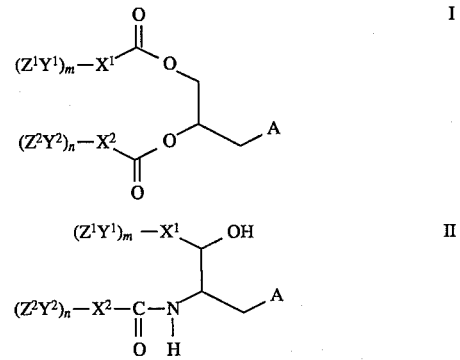

wherein,

A is a member selected from the group consisting of a serine radical, an ethanolamine radical, a choline radical, a phosphocholine radical, a phosphoserine radical, a phosphoethanolamine radical, a glycerol radical, a phosphoglycerol radical, an inositol radical, a phosphoinositol radical, $-NR^1R^2$, $-OCOR^3$, $-OH$, $-O-$glucose, $-O-$galactose and $-O-$oligosaccharide;

wherein, $R^1$ and $R^2$ are each members independently selected from the group consisting of H and lower alkyl; and $R^3$ is a member selected from the group consisting of alkyl radicals and unsaturated alkyl radicals;

$X^1$ and $X^2$ are each members independently selected from the group consisting of alkyl, unsaturated alkyl, alkyl linking group, and unsaturated alkyl linking group;

$Y^1$ and $Y^2$ are each members independently selected from the group consisting of $-S-$, $-NH-$, $-NHCO-$, $-CO(CH_2)_pCO_2-$, $-O-$, $=NNHCO-$, $-CO-$ and $-CO(CH_2)_pCONH-$, wherein p is an integer of from 0 to 8;

$Z^1$ and $Z^2$ are each independently a therapeutic agent; and m and n are each independently an integer of from 0 to 1, with the proviso that n+m is at least 1; and with the further provisos that when m is 0, $X^1$ is not a linking group, and when n is 0 that $X^2$ is not a linking group.

2. A pharmaceutical compound of claim 1 wherein said compound is of formula I, and A is a member selected from the group consisting of a phosphocholine radical, a phosphoserine radical, a phosphoethanolamine radical, a phosphoglycerol radical, and a phosphoinositol radical.

3. A pharmaceutical compound of claim 1 wherein said compound is of formula I and A is a member selected from the group consisting of $-OCOR^3$, $-O-$glucose, $-O-$galaclose and $-O-$oligosaccharide.

4. A pharmaceutical compound of claim 1 wherein said compound is of formula I and A is $-NR^1R^2$.

5. A pharmaceutical compound of claim 2 wherein m is 0, $X^1$ is alkyl and $Z^2$ is a therapeutic agent selected from the group consisting of paclitaxel, doxorubicin and podophyllotoxin.

6. A pharmaceutical compound of claim 2 wherein n is 0, $X^2$ is alkyl and $Z^1$ is a therapeutic agent selected from the group consisting of paclitaxel, doxorubicin and podophyllotoxin.

7. A pharmaceutical compound of claim 3 wherein m is 0, $X^1$ is alkyl and $Z^2$ is a therapeutic agent selected from the group consisting of paclitaxel, doxorubicin and podophyllotoxin.

8. A pharmaceutical compound of claim 3 wherein n is 0, $X^2$ is alkyl and $Z^1$ is a therapeutic agent selected from the group consisting of paclitaxel, doxorubicin and podophyllotoxin.

9. A pharmaceutical compound of claim 4 wherein m is 0, $X^1$ is alkyl and $Z^2$ is a therapeutic agent selected from the group consisting of paclitaxel, doxorubicin and podophyllotoxin.

10. A pharmaceutical compound of claim 4 wherein n is 0, $X^2$ is alkyl and $Z^1$ is a therapeutic agent selected from the group consisting of paclitaxel, doxorubicin and podophyllotoxin.

11. A pharmaceutical composition comprising a compound selected from the group consisting of compounds of formula I and compounds of formula II:

wherein,

A is a member selected from the group consisting of a serine radical, an ethanolamine radical, a choline radical, a phosphocholine radical, a phosphoserine radical, a phosphoethanolamine radical, a glycerol radical, a phosphoglycerol radical, an inositol radical, a phosphoinsitol radical, $-NR^1R^2$, $-OCOR^3$, $-OH$, $-O-$glucose, $-O-$galactose and $-O-$oligosaccharide;

wherein, $R^1$ and $R^2$ are each members independently selected from the group consisting of H and lower alkyl; and $R^3$ is a member selected from the group consisting of alkyl radicals and unsaturated alkyl radicals;

$X^1$ and $X^2$ are each members independently selected from the group consisting of alkyl, unsaturated alkyl, alkyl linking group, and unsaturated alkyl linking group;

$Y^1$ and $Y^2$ are each members independently selected from the group consisting of $-S-$, $-NH-$, $-NHCO-$, $-CO(CH_2)_pCO_2-$, $-O-$, $=NNHCO-$, $-CO-$ and $-CO(CH_2)_pCONH-$, wherein p is an integer of from 0 to 8;

$Z^1$ and $Z^2$ are each independently a therapeutic agent; and m and n are each independently an integer of from 0 to 1, with the proviso that n+m is at least 1, and with the further provisos that when m is 0 that $X^1$ is not a linking group, and when n is 0 that $X^2$ is not a linking group, in a micellar formulation.

12. A pharmaceutical composition of claim 11 wherein said micellar formulation comprises a member selected from the group consisting of lysophosphatidylcholine, lysophosphatidylethanolamine, lysophosphatidylserine, lysophosphatidylglycerol, acyl-polyoxyethylene esters, alkyl-polyoxyethylene ethers, phosphatidylethanolamine-polyoxyethylene conjugates, phosphatidic acid-polyoxyethylene conjugates and octyl glucopyranoside.

13. A pharmaceutical composition of claim 11 wherein said micellar formulation comprises 1-stearoyl-L-α-phosphatidylcholine.

14. A pharmaceutical composition of claim 11 wherein said compound is 1-oleoyl-2-(N-(4 '-O-(2"-taxyl)-succinoyl)- 11-aminoundecanoyl)-L-α-phosphatidylcholine and said micellar formulation comprises 1-stearoyl-L-α-phosphatidylcholine.

15. A pharmaceutical composition comprising a compound selected from the group consisting of compounds of formula I and compounds of formula II:

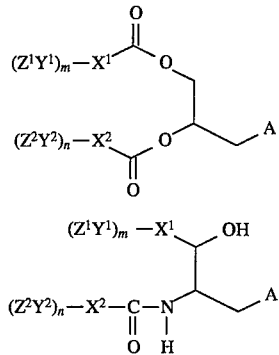

wherein,

A is a member selected from the group consisting of a serine radical, an ethanolamine radical, a choline radical, a phosphocholine radical, a phosphoserine radical, a phosphoethanolamine radical, a glycerol radical, a phosphoglycerol radical, an inositol radical, a phosphoinositol radical and $-NR^1R^2$, $-OCOR^3$, hydrogen, —O—glucose, —O—galactose and —O—oligosaccharide;

wherein, $R^1$ and $R^2$ are each members independently selected from the group consisting of H and lower alkyl; and $R^3$ is a member selected from the group consisting of alkyl radicals and unsaturated alkyl radicals;

$X^1$ and $X^2$ are each members independently selected from the group consisting of alkyl, unsaturated alkyl, alkyl linking group, and unsaturated alkyl linking group;

$Y^1$ and $Y^2$ are each members independently selected from the group consisting of —S—, —NH—, —NHCO—, $-CO(CH_2)_pCO_2-$, —O—, =NNHCO—, —CO— and $-CO(CH_2)_pCONH-$, wherein p is an integer of from 0 to 8;

$Z^1$ and $Z^2$ are each independently a therapeutic agent; and m and n are each independently an integer of from 0 to 1, with the proviso that n+m is at least 1, and with the further provisos that when m is 0 that $X^1$ is not a linking group, and when n is 0 that $X^2$ is not a linking group, in a liposomal formulation.

16. A pharmaceutical composition of claim 15 wherein said liposomal formulation comprises a member selected from the group consisting of phosphatidylcholine, phosphatidylethanolamine, phosphatidylserine, phosphatidylglycerol, phosphatidylinositol, cholesterol, diglycerides, ceramides, phosphatidylethanolamine-polyoxyethylene conjugates and phosphatidic acid-polyoxyethylene conjugates.

17. A pharmaceutical composition of claim 15 wherein said liposomal formulation comprises egg phosphatidylcholine.

18. A pharmaceutical composition of claim 15 wherein said liposomal formulation comprises egg phosphatidylcholine and 1-stearoyl-L-α-phosphatidylcholine.

19. A pharmaceutical composition of claim 15 wherein said compound is 1-oleoyl-2-(N-(4'-O-(2"-paclitaxyl)-succinoyl)- 11-aminoundecanoyl)-L-α-phosphatidylcholine and said liposomal formulation comprises egg phosphatidylcholine and 1-stearoyl-L-α-phosphatidylcholine.

* * * * *